Aug. 24, 1976 R. PINKUS Plant Pat. 3,948
PEPEROMIA PLANT (PINK GLOW)
Filed Aug. 27, 1975
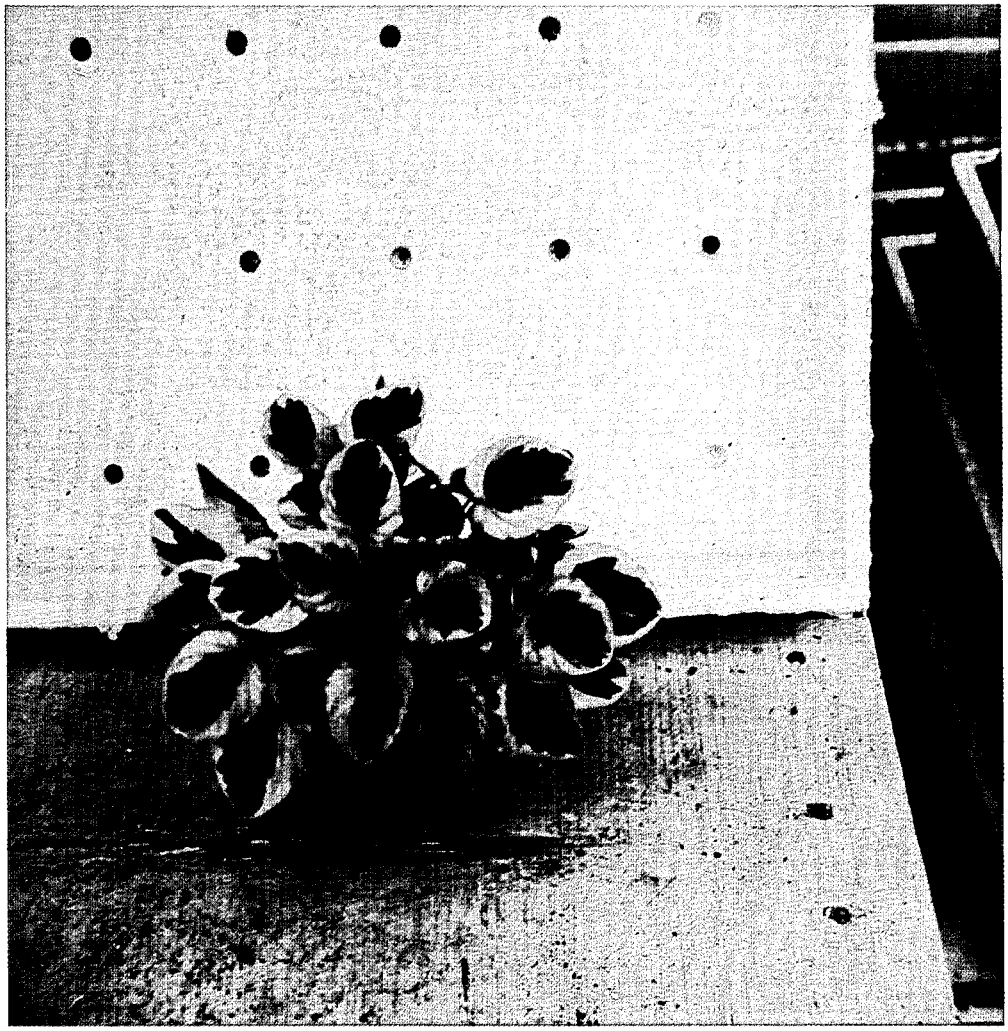

United States Patent

Plant Pat. 3,948
Patented Aug. 24, 1976

3,948

PEPEROMIA PLANT (PINK GLOW)

Ralph Pinkus, 7700 Northaven Road, Dallas, Tex. 75230

Filed Aug. 27, 1975, Ser. No. 608,382
Int. Cl.[2] A01H *5/00*
U.S. Cl. Plt.—88 1 Claim

BACKGROUND OF THE NEW PLANT

This plant is a mutant of *Peperomia grisea-argentea* variety "Blackie." The mutation occurred in our greenhouse in Dallas, Tex. The first mutation was propagated asexually and was very variable in the foliage colors. Many leaves were similar to those of the original variety.

By constant propagation and selection of the mutation I was able to select out over fifty (50) plants that are all uniform and now being propagated asexually and coming true to form.

Occasionally, in the large group of plants I now have, one will revert to the green foliage form.

We are enclosing a photograph of our stock of plants showing how we have fiinally stabilized this variety.

DESCRIPTION OF THE DRAWING

This new variety of Peperomia plant is illustrated by the accompanying full color photographic drawing which shows the plant at a mature stage of growth. The leaf coloration shown is believed to be as nearly true as it is reasonably possible to obtain by conventional professional photographic standards and procedures.

DESCRIPTION OF THE PLANT

The following is a detailed description of my new variety of Peperomia plant with color specification according to Exotica Third Horticultural Color Guide published by Roehrs Company, Rutherford, N.J., the observations having been made at Dallas, Tex.

The plant

Origin: Mutation.
Parentage: *Peperomia grisea-argentea.*
Classification: Piperaceae.
Form: Herbaceous.
Height: 6 inches.
Growth: Low, bushy house plant.
*Stem size.*—2 to 6 inches in length and ¼ inch at base. Basal stems which are very close to the ground.
Foliage: Quantity—abundant. One (1) leaflet per stem. Petiole arises from basal stem.

*Leaf size.*—On any one plant the leaves are generally 1 inch to 2 inches long and 1 inch to 1.5 inches wide.
*Leaf shape.*—Cordate, undulate at margins, occasionally dentate.. Glossy at first, pinkish bronze changing to metallic gray. Lighter on undersurface. Quilted leaf.
*Ribs & Veins.*—Pronounced on under side. Palmate.
*Rachie.*—Normal.
Color:
*Upper side.*—Meadow Green, #76, center with Carmine Red, #31+, extending out to a Creamy White, #1, margin and a Camellia, #31—, band along the margin.
*Under side.*—Seafoam Green, #71, center Creamy White, #1, margin.

The flower

Blooming habit: January to April.
Borne: Unbranched spike.
Size: Spike 6 inches to 8 inches tall.
Shape: Spike erect.
Petalage: Insignificant.
*Texture.*—Slightly sticky.
*Appearance.*—Spike pendulous when past.
*Persistence.*—After about three weeks, spike drops off.
Petaloids: Apetalous.
Discoloration. None.
Fragrance: None.

This new variety of Peperomia plant most nearly resembles the *Peperomia griseo-argentea* variety "Blackie." It differs from the "Blackie" variety in that instead of the leaves being green, they vary from a pale green center with a white margin to a deep rose center with a pink band along the margin.

This plant is a foliage plant. The variety of shades of coloring on the various leaves give this plant an unusual attractiveness.

I claim:

1. A new and distinctive variety of Peperomia plant substantially as herein shown and described, characterized by the unique combination of pink and white stripes and bronze appearance in the center of the leaf.

No references cited.

ROBERT E. BAGWILL, Primary Examiner